United States Patent
Masson et al.

(10) Patent No.: US 11,185,699 B2
(45) Date of Patent: Nov. 30, 2021

(54) SYSTEMS AND METHODS FOR GENERATING THERAPEUTIC ELECTRIC FIELDS FOR CAPTURE OF NERVOUS SYSTEM TARGETS

(71) Applicant: NUXCEL Limited, Dublin (IE)

(72) Inventors: Stephen C Masson, Raleigh, NC (US); Michael Cuchiara, Durham, NC (US); Jean Darnieder, Durham, NC (US)

(73) Assignee: NuXcel Limited, Dublin (IE)

( * ) Notice: Subject to any disclaimer, the term of this patent is extended or adjusted under 35 U.S.C. 154(b) by 141 days.

(21) Appl. No.: 15/786,536

(22) Filed: Oct. 17, 2017

(65) Prior Publication Data

US 2020/0269052 A1    Aug. 27, 2020

Related U.S. Application Data

(63) Continuation of application No. PCT/US2016/027363, filed on Apr. 13, 2016.

(60) Provisional application No. 62/146,802, filed on Apr. 13, 2015.

(51) Int. Cl.
*A61N 1/36* (2006.01)
*A61N 1/375* (2006.01)

(52) U.S. Cl.
CPC ...... *A61N 1/36185* (2013.01); *A61N 1/36117* (2013.01); *A61N 1/36135* (2013.01); *A61N 1/36182* (2013.01); *A61N 1/37516* (2017.08)

(58) Field of Classification Search
CPC .. A61N 1/0551; A61N 1/056; A61N 1/36114; A61N 1/36117; A61N 1/36135; A61N 1/36182; A61N 1/36185; A61N 1/37516
See application file for complete search history.

(56) References Cited

U.S. PATENT DOCUMENTS

| | | |
|---|---|---|
| 2006/0253182 A1* | 11/2006 | King ............... A61N 1/0551 607/117 |
| 2010/0228310 A1 | 9/2010 | Shuros et al. |
| 2011/0040547 A1 | 2/2011 | Gerber et al. |
| 2012/0071936 A1 | 3/2012 | Pianca et al. |
| 2013/0085545 A1 | 4/2013 | Mashiach |
| 2013/0131743 A1 | 5/2013 | Yamasaki et al. |
| 2014/0142590 A1 | 5/2014 | Masson |
| 2014/0227739 A1 | 8/2014 | Spodsberg |

(Continued)

FOREIGN PATENT DOCUMENTS

| | | |
|---|---|---|
| JP | 2010516353 A | 5/2010 |
| WO | 2008092246 A1 | 8/2008 |

OTHER PUBLICATIONS

International Search Report and Written Opinion for PCT/US16/27363.

(Continued)

*Primary Examiner* — Amanda K Hulbert

(57) ABSTRACT

A neuromodulation system includes neuromodulation electrodes on an electrode support that is positionable within a blood vessel for transvascular stimulation of target nerves. Cathode surface area, cathode-to-anode spacing, and other parameters are selected for capture of specific types of nerves (sympathetic, parasympathetic, and/or mixed nerves), nerves located at larger or shorter distances from the vascular wall, and also for proper nerve capture for the targeted types of nerves.

7 Claims, 11 Drawing Sheets

(56) References Cited

U.S. PATENT DOCUMENTS

2015/0012070 A1    1/2015   Hoffer
2015/0039058 A1    2/2015   Masson et al.
2015/0045810 A1*   2/2015   Hoffer .................. A61N 1/3601
                                                                                    606/129

OTHER PUBLICATIONS

Office Action for Japanese Application 2017-553423.
Examination Report for Australian Application 2016248118.
Supplemental European Examination Report for EP 16836078.2.

* cited by examiner

KEY:
OPEN FILL = UN-ENERGIZED
SOLID FILL = ANODE OR CATHODE
DIAGONAL HATCH FILL = ANODE OR CATHODE

REGIONS CONTAINING POSSIBLE OBSTRUCTIONS

SYSTEMS AND METHODS FOR GENERATING THERAPEUTIC ELECTRIC FIELDS FOR CAPTURE OF NERVOUS SYSTEM TARGETS

This application is a continuation in part of PCT/US2016/027363, filed Apr. 13, 2016, which claims the benefit of U.S. Provisional Application No. 62/146,802, filed Apr. 13, 2015, each of which is incorporated herein by reference.

TECHNICAL FIELD OF THE INVENTION

The present application generally relates to systems and methods for capturing nervous system targets using electrical energy. More specifically, the application relates to systems and methods for optimizing characteristics of a generated electric field in order to optimize capture of nervous system targets.

BACKGROUND

Co-pending U.S. application Ser. No. 13/547,031 entitled System and Method for Acute Neuromodulation, filed Jul. 11, 2012 (the "'031 application"), filed by an entity engaged in research with the owner of the present application, and U.S. application Ser. No. 14/642,699, filed Mar. 9, 2015 and commonly owned with the present application (the "699 application") and U.S. application Ser. No. 14/820,536, filed Aug. 6, 2015 (the "'536 application") describe systems that may be used for hemodynamic control in the acute hospital care setting, or for other purposes, by transvascularly directing therapeutic stimulus to nervous system targets (e.g. parasympathetic nerves and/or sympathetic cardiac nerves) using one or more therapeutic elements (e.g. electrodes or electrode arrays) positioned in the neighboring vasculature. In some methods of transvascular nerve capture, including some described in the '031 application, therapy may be delivered using therapeutic elements positioned in a blood vessel so as to capture parasympathetic nerves and/or sympathetic cardiac nerves outside that vessel. In other methods of transvascular nerve capture, including some described in the '699 application, therapy may be delivered using multiple therapeutic elements positioned in different blood vessels. For example, one therapeutic element may be positionable within a first blood vessel so as to capture a first nervous system target outside the first blood vessel, and the other may be positionable in a second, different, blood vessel in order to capture a second nervous system target outside the second blood vessel.

A neuromodulation system used for such therapy may include an external pulse generator/stimulator that is positioned outside the patient's body. The therapeutic elements may be carried by one or more percutaneous catheters that are coupled to the external pulse generator. In other embodiments an implantable stimulator may instead be used, in which case the therapeutic elements may be disposed on leads electrically coupled to the implantable stimulator/pulse generator. The stimulator/pulse generator is configured to energize the therapeutic elements to transvascularly capture the target nerve fibers.

Commonly owned Publication No. WO 2016/022867, filed Aug. 6, 2015, shows and describes various features for use on electrode systems of the type used to transvascularly stimulate nerves located outside the vasculature by energizing one or more electrode pairs of the electrode system.

Each of the above-referenced applications is incorporated herein by reference.

The present application describes systems and methods that can help to optimize delivery of therapy to target nerves. While references will be made to electrodes on catheters used for acute systems intended for short-term use over a period of hours or days, modifications are contemplated in which the electrodes are on leads that are chronically implanted for longer term treatment. Thus, the term "catheter" is used here for convenience and is not intended in a limiting sense, since in each of the described embodiments the catheter can be replaced with an implantable lead.

DETAILED DESCRIPTION OF THE DRAWINGS

Figure 3:
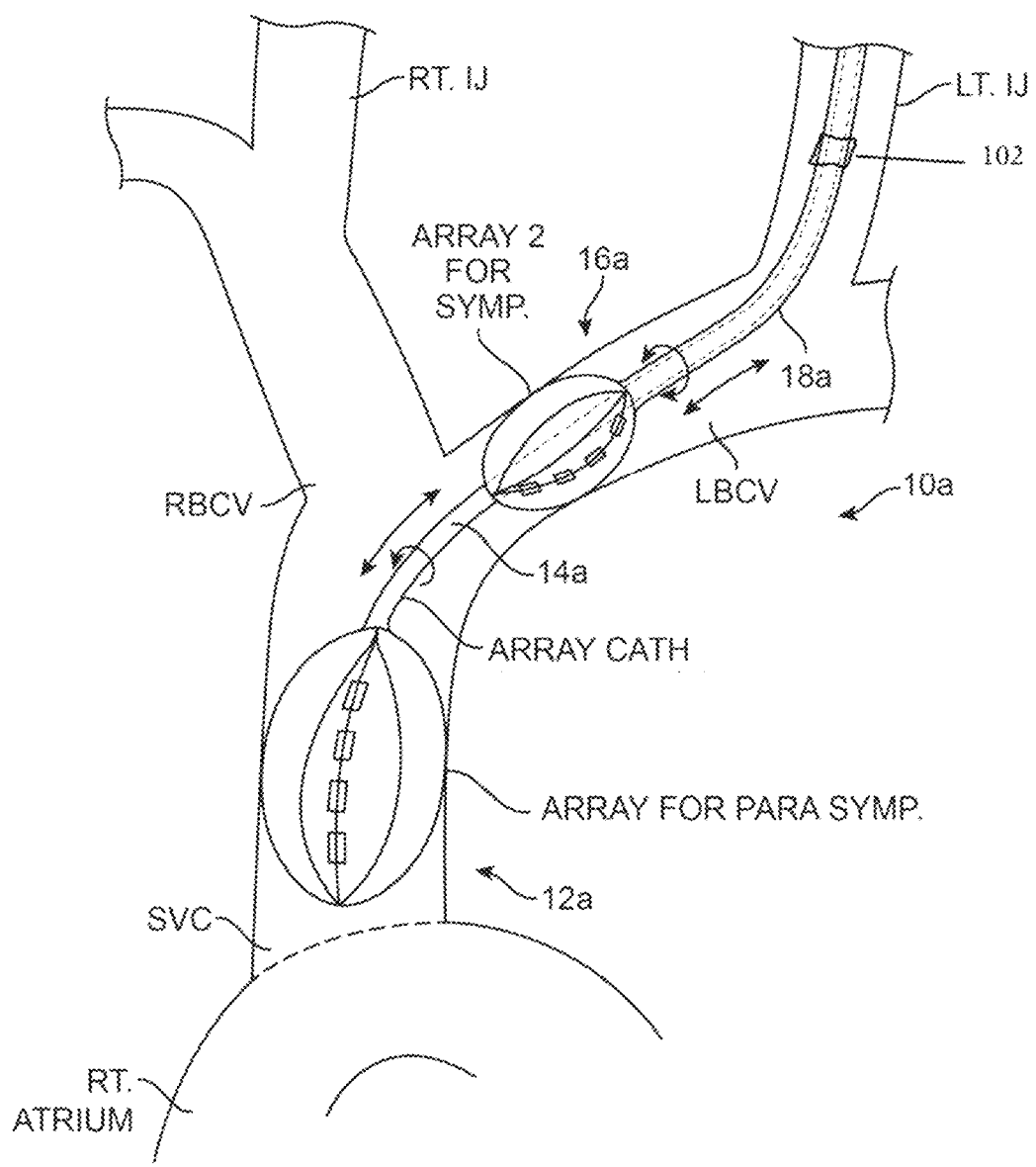

FIG. 3 schematically shows another catheter system with therapeutic elements positioned in the left brachiocephalic vein and superior vena cava.

Figure 4:
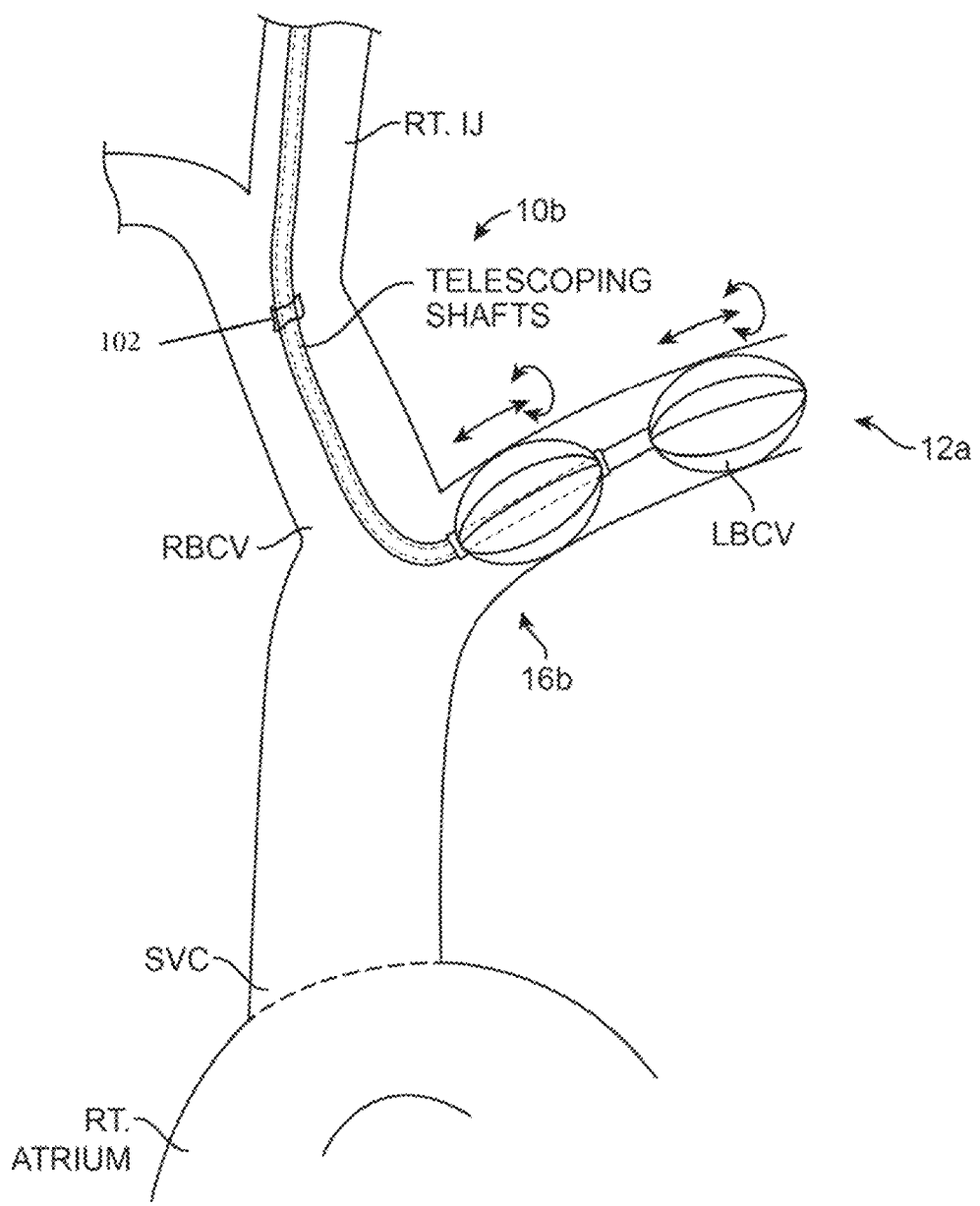

FIG. 4 schematically shows another catheter system with therapeutic elements positioned in the left brachiocephalic vein.

Figure 5A:
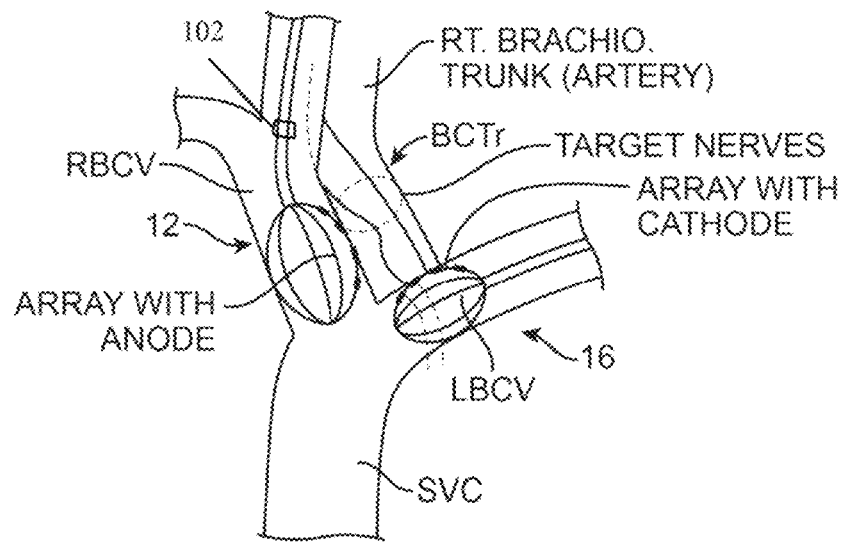
Figure 5B:
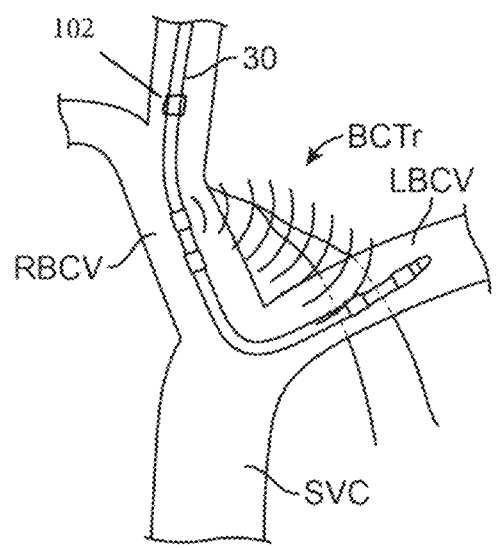
Figures 6A, 6B:
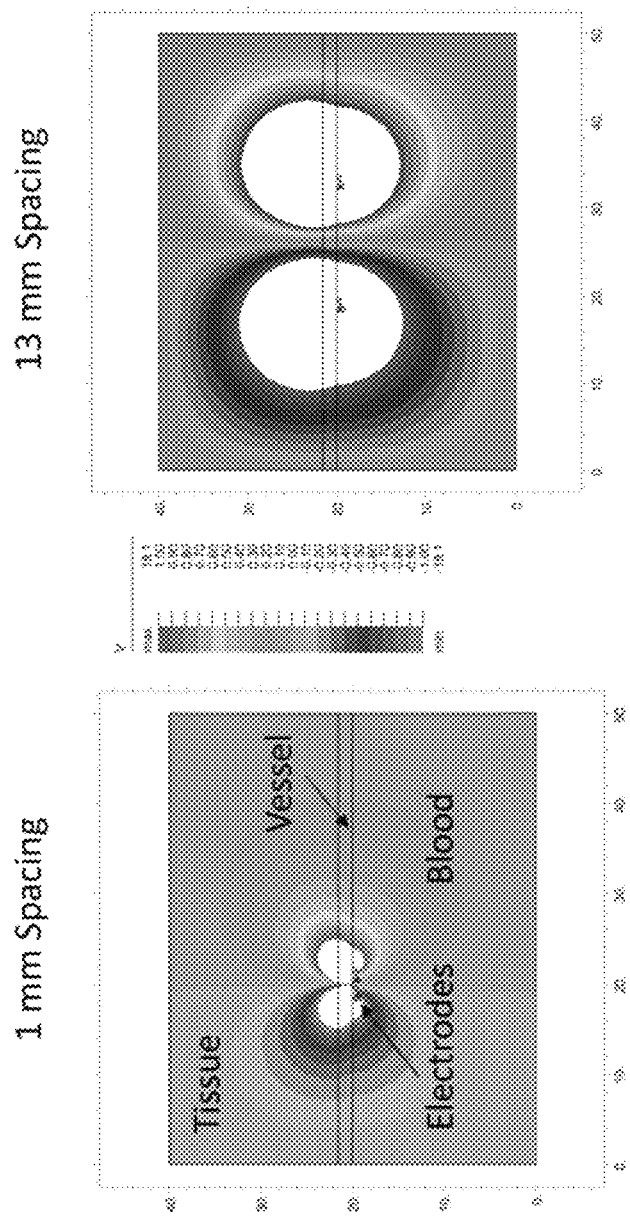
Figure 6C:
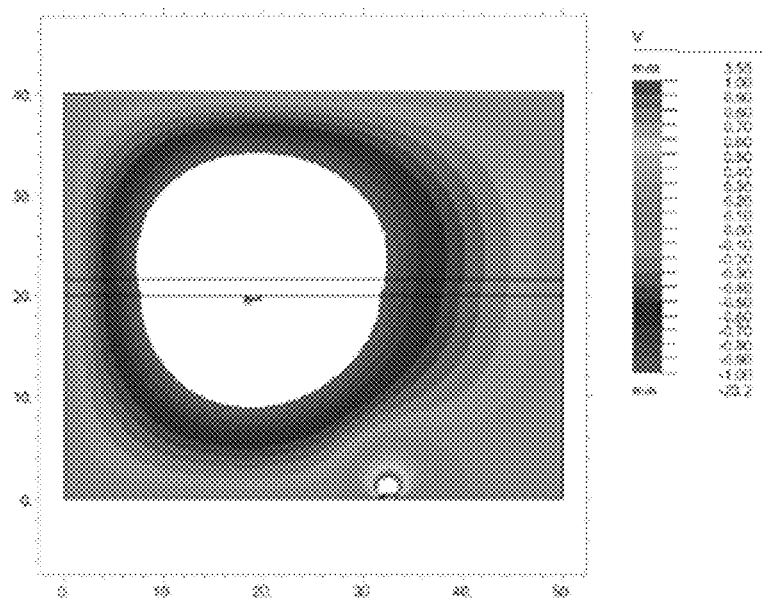

FIGS. 5A and 5B illustrate use of an anode in one vessel and a cathode in a second vessel to create an electric field that captures target nerves within the brachiocephalic triangle (BCTr).

FIGS. 6A, 6B, 6C and 7 graphically depict electric field models for systems incorporating certain of the identified electrode array characteristics.

Figure 8:
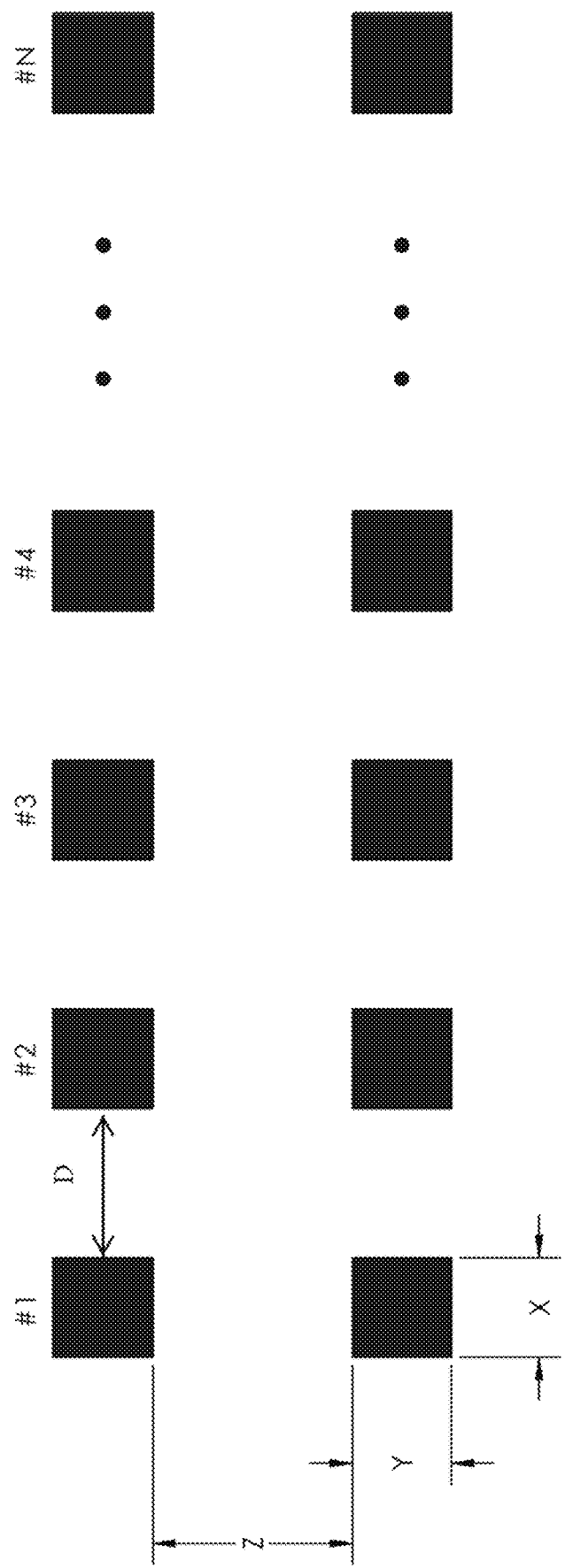

FIG. 8 depicts electrode array characteristics, including numbers of electrodes, electrode area, and electrode spacing in two directions.

FIGS. 9A-9F each illustrate an array of eight electrodes, and each shows an example of selective use of subsets of those electrodes as the cathode and anode for creating an electric field for stimulation.

Figure 10A:
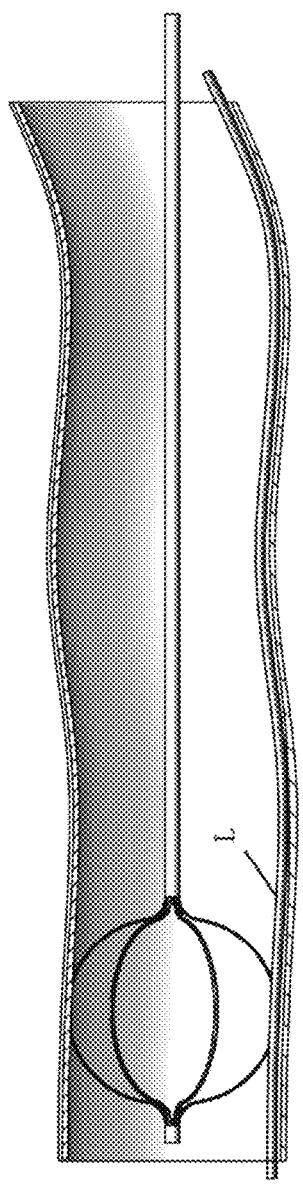
Figure 10B:
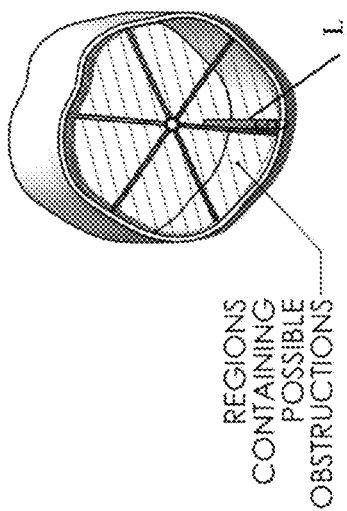

FIG. 10A is a partially cut-away side view of a blood vessel, and FIG. 10B is a cross-section view of the blood vessel. Each shows positioning of an electrode carrying member such that its struts contact the blood vessel wall on opposite sides of a CRM lead.

DESCRIPTION

Figure 1A:
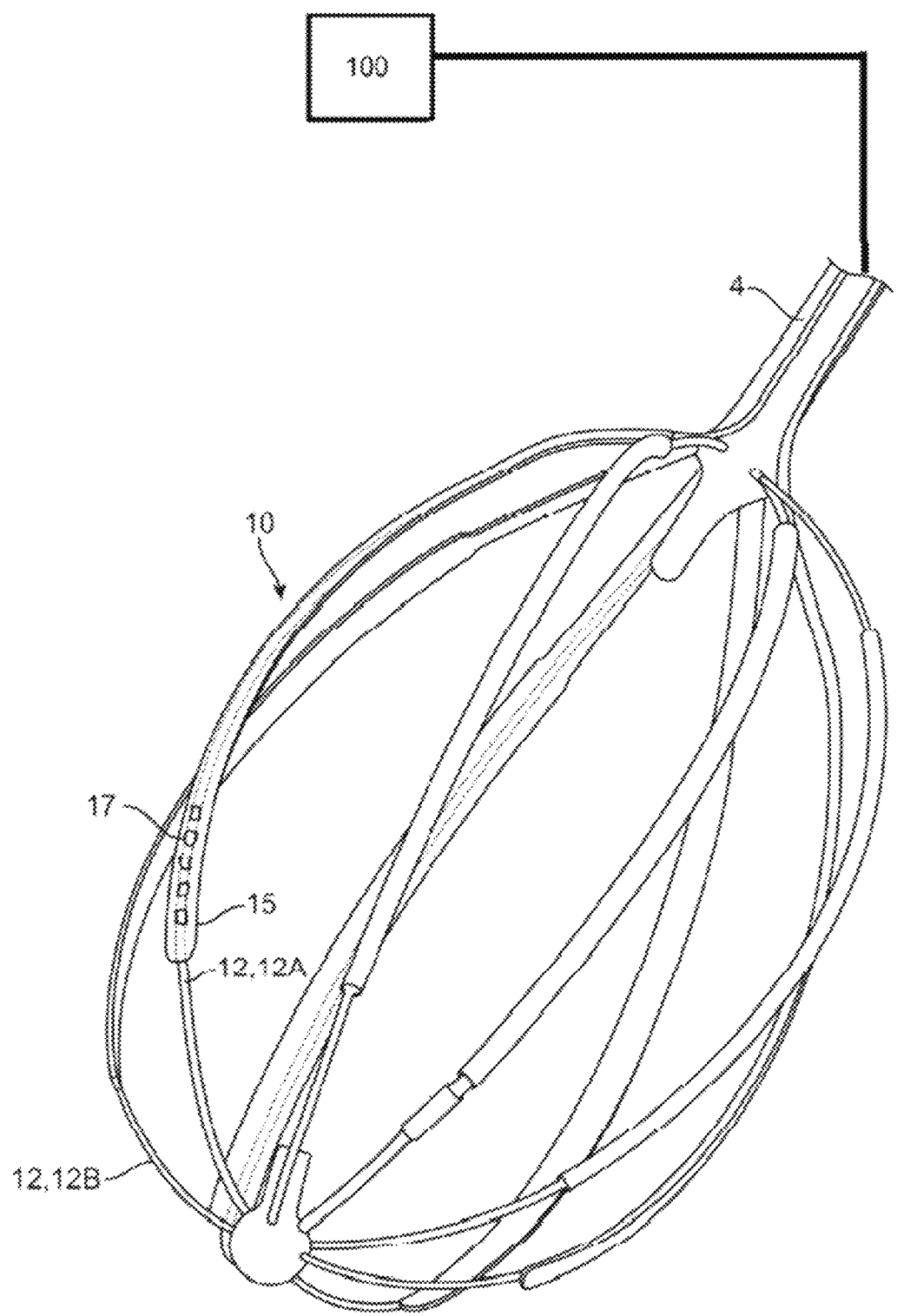
FIG. 1A shows an exemplary catheter system.

Referring to FIG. 1A, a system incorporating the features described herein is one having a pulse generator/stimulator 100 as well as a catheter. The catheter includes an electrode support 10 carrying one or more electrodes as described in the referenced applications. Each electrode support is positionable within a target blood vessel and expandable to place the electrodes into contact with the vascular wall. The pulse generator/stimulator 100 may be an external device that is positioned outside the patient's body, although in modified embodiments an implantable stimulator may instead be used, in which case each of the percutaneous catheter systems disclosed herein may be replaced with leads. When the stimulator is used to energize the electrodes (or select ones of the electrodes), an electric field is created that extends beyond the walls of the blood vessel so as to capture nerve targets located outside the blood vessel. The electrodes are shielded so as to minimize electrical conduction into the blood pool. The electrodes may be operated in a bipolar or a monopolar configuration.

One exemplary electrode support 10 (also referred to as an "electrode carrying member") 10 is shown in FIG. 1A. It should be appreciated that this support is shown by way of example, and that the concepts disclosed herein may be used in conjunction with supports having different configurations. Support 10 is positioned on the distal part of a catheter member 14. The electrode carrying member 10 includes a plurality of struts 12. One or more of the struts carries one or a plurality of electrodes 17. The support 10 is designed to bias such electrodes into contact with the vessel wall. The electrodes 17 may be carried by the struts 12 in a variety of ways. For example, the electrodes may be mounted to or formed onto a substrate 15 that is itself mounted onto a strut or a plurality of struts, or the struts might be flex circuits including the electrodes, or the electrodes might be formed or deposited directly onto the struts. The material forming the struts 12 may have a shape set or shape memory that aids in biasing the circumferentially-outward facing surfaces (and thus the electrodes) against the vessel wall. The struts 12 or substrates 15 might utilize materials or coatings that allow the electrodes' active surfaces (those intended to be placed against the vascular wall) to be exposed, but that insulate the remainder of each electrode's surface(s) against loss of stimulation energy into the blood pool. In some embodiments, the struts 12 or substrate may be formed of an insulative substrate such as a polymer (including silicone, polyurethanes, polyimide, and copolymers) or a plastic.

Figure 1B:
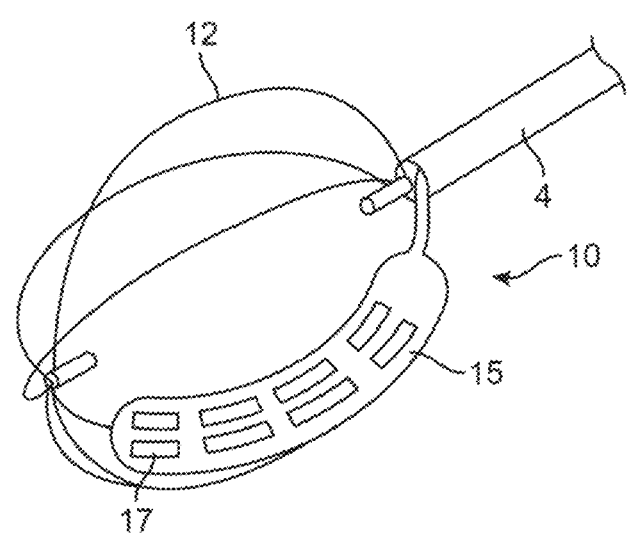
FIG. 1B shows a modified version of the electrode support of the system of FIG. 1A FIG. 2 schematically shows electrode supports of an alternative system positioned with therapeutic elements in the left brachiocephalic vein (LBCV) and the superior vena cava (RB CV).
Figure 2:
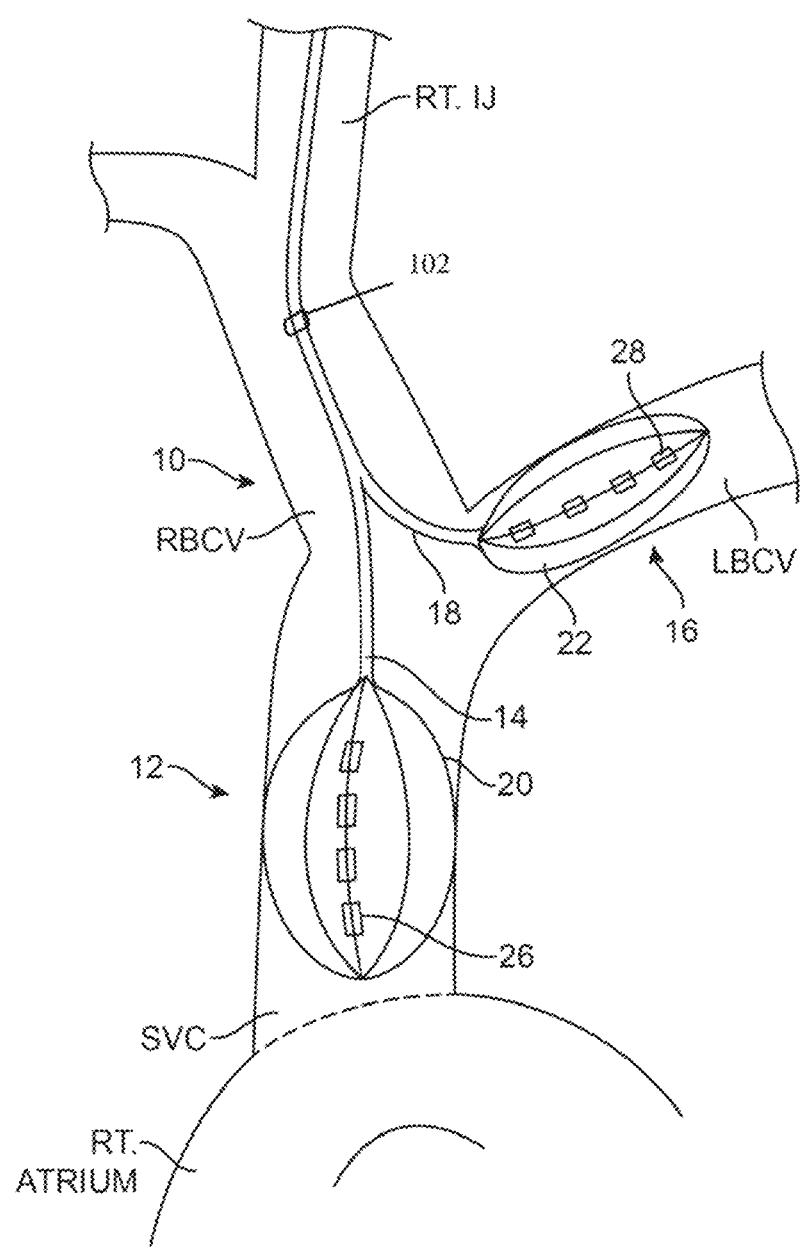

The electrodes can be constructed onto the strut or substrate using a variety of manufacturing techniques, including subtractive manufacturing processes (such as mechanical removal by machining or laser cutting), additive processes (such as laser sintering, deposition processes, conductor overmolding), or combinations (such as printed circuit technology with additive plating). In some embodiments, the struts and electrodes may be flex circuit or printed circuit elements. FIG. 1A shows that the electrodes on one strut might be arranged longitudinally in a single column. FIG. 1B shows that the electrodes on a strut might be arranged in a plurality of columns and rows. In each case, electrodes may be carried on multiple struts of the support. These embodiments as well as those described below may be configured for bipolar use, with some of the electrodes functioning as cathodes and others functioning as anodes. They may also be configured for monopolar use, by incorporating an anode 102 mounted on the catheter shaft as described with respect to the FIG. 2-5B configurations.

Other electrode support configurations, suitable for positioning electrodes in multiple blood vessels, are shown in FIGS. 2-5B. The details of these embodiments, and details of the illustrated anatomical region as well as other desirable regions for electrode positioning and nerve capture, are found in the '699 application which is incorporated herein by reference. These configurations are suitable for bipolar use, but in the attached drawings the embodiments are modified to include indifferent electrodes 102 on the electrode support (e.g. on the shaft of the catheter or lead to which the support is mounted) allowing the electrodes to be used in a monopolar configuration. In these embodiments, the indifferent electrodes are shown on the catheter shaft such that they are disposed within the blood pool during use. In these embodiments, the electrode in the blood pool may be used as the anode and the electrode positioned against the vessel wall may be used as the cathode, or vise versa. Various other configurations may be used for the catheters, electrode supports, and electrodes, and those from the '699 application are shown only for purposes of illustration.

Described herein are characteristics that may be incorporated into a neuromodulation system to create an electric field having desired properties. In this description, the portion of an electric field that has electrical properties that will capture a target nerve will be referred to as the "capture portion." The desired properties that may be achieved using one or more of the characteristics include dimensional properties of the capture portion, such as the depth of capture portion ("capture depth") and the width of the capture portion ("capture width"). Relating to the capture depth and/or capture width is the "nerve capture specificity", or the ability to generate a capture portion in the region of the nerve target while minimizing the amount of capture portion extending outside the region of the nerve target. Other desired properties might be the ability to preferentially capture small-diameter nerves without capturing large-diameter nerves ("small nerve specificity"), or the ability to preferentially capture large-diameter nerves without capturing small-diameter nerves ("large nerve specificity"). Yet another desired property is the magnitude of the physiologic response as determined using feedback from physiologic sensors on the patient or in the patient's vasculature. A determination of physiologic response may be based on values of sensed or derived patient parameters, such as central venous pressure (CVP), pulmonary capillary wedge pressure (PCWP), cardiac index, cardiac output, derivations of vascular resistance, heart rate, blood pressure (arterial).

Figure 7:
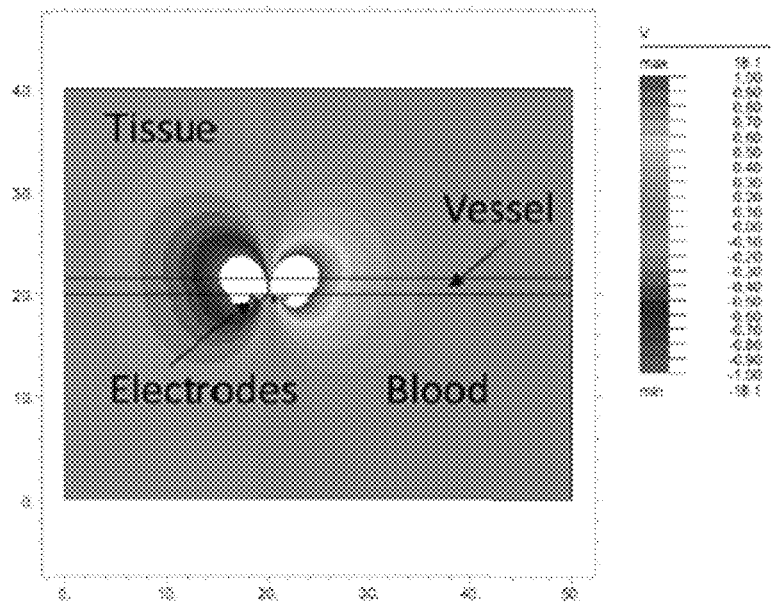

FIGS. 6 and 7 depict electric field models for systems incorporating certain of the identified characteristics. In these figures, electrodes are schematically illustrated in contact with the inner surface of the wall of the blood vessel (shown in cross-section) within which the electrodes are positioned. In these drawings, the white region functions as a marker for depth (in the vertical direction) and width (in the horizontal direction). The neuromodulation system characteristics that can be used (individually or in combination) to achieve the desired electric field properties include the following:

Electrode size—the surface area of the active face of the cathode electrode in contact with the vascular wall. The anode may be the identical size, or a different size, such as in a monopolar configuration. In general, a larger electrode size will produce an electric field having a larger capture depth, a larger capture width, decreased nerve capture specificity and an equivalent magnitude of physiologic response compared with a smaller sized electrode used under otherwise identical conditions. FIG. 7 illustrates a field model for an electrode having a 1 mm×1 mm active surface. A field model for an electrode having a larger surface area would show white regions that are larger in both the vertical (depth) and horizontal (width) directions. Small and large nerve specificity might also be impacted by differences in electrode size. A range of suitable electrode sizes for therapeutic applications of the type described in the referenced applications is approximately 0.5 $mm^2$-10 $mm^2$, preferably in the range of 3 $mm^2$-10 $mm^2$, and most preferably in the range of 5 $mm^2$-10 $mm^2$. Note that the electrodes may have various shapes, including the rectangular or square shapes shown, other polygonal shapes, circular, elliptical, etc.

Electrode spacing or separation distance—the edge-to-edge spacing between active electrodes. More particularly, this relates to the spacing between active electrodes of opposite polarity in a bipolar system, or the spacing between the active and indifferent electrodes in a monopolar system. In FIG. 6, the electric field model on the left simulates use of a bipolar arrangement using a 1 mm spacing, and the one on the center simulates use of a bipolar arrangement using a 13 mm spacing. As shown, increasing electrode spacing creates a wider and deeper electric field. A monopolar arrangement such as those with the indifferent electrode in the blood pool as shown in the drawings creates a significantly wider and deeper electric field. These progressions to a larger electrode spacing also decrease the specificity of the field. Moreover, an electrode field generated using electrodes having greater electrode spacing will preferentially capture larger diameter nerves, while an electric field generated using electrodes having a smaller electrode spacing will preferentially capture small diameter nerves. Where parasympathetic nerves and/or cardiac sympathetic nerves are targeted for the type of therapy described in the above-referenced applications, the parasympathetic nerve fibers would be considered large nerves and the cardiac sympathetic nerves fibers would be considered small nerves. A suitable range of electrode spacing for such therapeutic applications is approximately 0.5 mm-10 mm or 0.05-15 mm. Wide spacing has shown particularly beneficial with large surface area electrodes (e.g. electrodes in the surface area range of 3 $mm^2$-10 $mm^2$). Suitable wide spacing distances for electrodes in that size range are in the range of 1.5-15 mm, and more preferably in the range of 2.25 mm-10 mm. Note that in many cases electrode spacing will not be uniform either due to the design of the electrode support or as a result of variations in blood vessel diameter.

Stimulation Waveform, such as whether a balanced or unbalanced biphasic waveform is utilized, can impact the magnitude of the physiologic response. In particular, a balanced biphasic waveform will give a greater physiologic response than will an unbalanced biphasic waveform when all other parameter are identical.

Electrical Parameters—such as current amplitude and pulse width. These can be varied to vary the capture depth, capture width, and nerve capture specificity. As one example, increasing the output current increases the capture depth.

Selection of the disclosed parameters can also be used to target certain types of nerves. More specifically, small surface area electrodes with smaller spacing may be used to capture "independent nerves" (nerves that are either parasympathetic or sympathetic), while larger spacing/larger electrodes can be used to capture "mixed nerves". The term "mixed nerves" is used here to refer to the common nerve bodies formed by parasympathetic and sympathetic nerves that anastamose as they extend towards the cardiac plexus, and also independent parasympathetic and cardiac sympathetic nerves that coexist in a particular area.

Smaller spacing with smaller electrodes can be used give increased "specificity" of capture compared with capture that can be achieved using larger spacing and larger electrodes. This means the ability to differentiate parasympathetic and sympathetic nerves that run in close proximity to each other in order to capture one type preferentially over the other type. This is especially true in the area of, or approaching near, the cardiac plexus, where the different nerve types come together.

FIG. 8 schematically illustrates the variations that may be achieved with an array of electrodes. In this drawing, two rows of electrodes are shown. If the electrode support includes struts (e.g. such as the FIGS. 1A and 1B embodiments), each row might extend longitudinally on a different strut as in FIG. 1A, or both rows might be on the same strut as in FIG. 1B. Parameters that may be selected depending on the desired properties of the electric field include the electrode area (which, in the case of the illustrated square or rectangular electrodes, is the length X times the width Y), the lateral distance Z between the electrodes, the longitudinal distance D between the electrodes, and the number N of electrodes in the row(s). In some embodiments the array is configured such that the longitudinal direction is generally parallel to the direction of blood flow of the vessel. Preferred configurations will have arrays of between 2-16 active electrodes. Where rows of electrodes are formed on separate struts, the lateral distance Z may be a function of the circumferential spacing between those struts. Note that this arrangement results in relatively wide electrode spacing such as spacing in the ranges discussed above, and it facilitates positioning of the electrodes around interfering structures within the blood vessel, such as other medical devices, scarring, venous valves, etc. FIGS. 10A and 10B show electrode carrying struts positioned on opposite sides of a cardiac rhythm management ("CRM") leads L extending through a blood vessel.

Figure 9A:
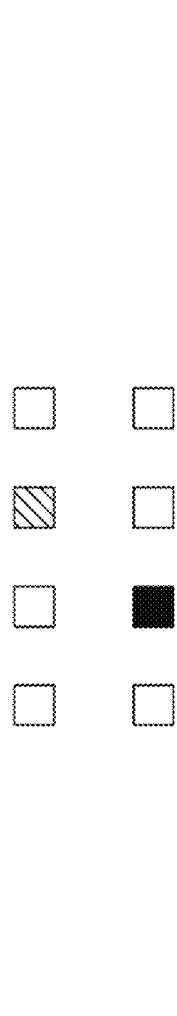
Figure 9B:
Figure 9D:
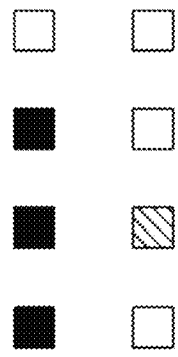
Figure 9C:
Figure 9F:
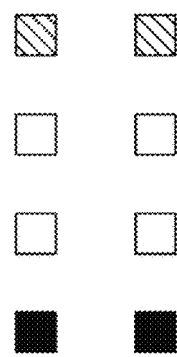
Figure 9E:

The electrode size and spacing characteristics can be achieved by physically building the electrodes to have the required size and spacing to achieve the desired properties, or the characteristics may be achieved through programming of the stimulator 100. For example, a system may be programmed to energize a single electrode (e.g. 1 mm×1 mm or some other size) when electric field properties achieved from an electrode of that size are desired (see, e.g. FIGS. 9(a) and 9(b) in which one electrode is used as an anode, another electrode is used as an cathode, and the remaining electrodes are left inactive). Note that the active electrodes may be laterally positioned related to one another as in FIG. 1(a) (on the same or different struts), or diagonally positioned as in FIG. 1(b) for greater spacing. They might also be longitudinally adjacent, (not shown—but consider active use of two of the electrodes visible in FIG. 1A). The system might also be programmed to simultaneously energize a collection of those electrodes, causing them to function as if they were a single electrode, when electric field properties achieved from a larger surface area electrode are desired. For example, in FIGS. 9(e) and 9(f), a pair of laterally spaced electrodes forms the anode and a separate pair of laterally spaced electrodes forms the cathode, and in FIG. 9(c) three active electrodes form the cathode and three form the anode. As illustrated in FIG. 9(d), in some cases the number of electrodes activated to form the anode might be larger or smaller than the number of electrodes activated to form the cathode. Note that the term "surface area," when used with respect to a collection of physical electrodes operated together to function as a single cathode, means the combined surface area of the active electrodes functioning as the cathode. In FIG. 9(d), for example, the surface area of the virtual electrode formed by simultaneous activation of the three black physical electrodes is the sum of the surface area of the three black physical electrodes. Note that a virtual electrode may be formed by simultaneously activation of physical electrodes carried on a common member (e.g. on the same strut of the illustrated electrode support) or on different members (e.g. on different struts of the illustrated electrode support).

Similarly, the catheter may be constructed so that the electrodes are physically spaced using the spacing that will give the electric field the desired properties, or the system may be programmed to selectively energize electrode pairs in a larger array that are spaced by the desired spacing (e.g.

in a longitudinal array of four electrodes, energizing the first and second electrodes if closer spacing is needed, and energizing the first and fourth electrodes if greater spacing is needed). Looking again at FIG. 9(d), the "electrode spacing" for this embodiment is determined by measuring the shortest distance between an edge of the active electrode on the left (formed by the three black physical electrodes) and an edge of active electrode (the hatched physical electrode) on the right.

Note also that while the FIG. 9(a)-(f) arrays have individual physical electrodes physically constructed to have uniform size and uniform spacing, other arrays might have one or more regions with different characteristics. For example, a first region might be provided to have electrodes with a first surface area and/or a first electrode spacing distance, and a second region might have electrodes with a second surface area and/or a second electrode spacing distance, where either or both of the surface area and/or electrode spacing used in the second region differs from that used in the first region.

Methods of using such systems may be employed to aid in mapping procedures performed to ensure optimal catheter placement for capturing target nerves. For example, certain of the listed characteristics described above may be employed in a catheter positioning and mapping procedure by generating broad electric fields and looking for a desired physiologic response to discover whether the nerves whose capture would achieve the desired physiologic response would fall within the capture portion of the electric field generated by electrodes on the catheter. If the desired physiologic response is not achieved with the catheter in the current position, the catheter is repositioned. If the desired physiologic response is achieved, the catheter position is maintained and therapy is delivered using the same characteristics that were used for mapping, or the characteristics are altered to narrow the field to increase the specificity of the therapy at the target nerves or to preferentially select large- or small-diameter nerves for therapy or to modulate physiologic response.

As another example, a first mapping step might generate a broad and shallow field to determine whether "near field" or "close distance" nerves (close to the vessel wall, such as less than 1 mm away from the wall) can be captured using electrodes in the current catheter position, and a second mapping step might generate a deeper and wider field to determine whether "far field" or "long distance" nerves (further from the vessel wall, such as further than 1 mm away from the wall) can be captured from the catheter site. If the desired physiologic response is not achieved with the catheter in the current position, the catheter is repositioned. If the desired physiologic response is achieved using the close distance or long distance stimulus, the catheter position is maintained and therapy is delivered with the stimulus that generated the physiologic response. The therapy can be one that delivers either the broad and shallow field to capture the close distance nerves or the deeper and wider field to capture the long distance nerves, or it can be one that alternates a broad/shallow mode for capture of the close distance nerves duty cycled with a with a deep/wide mode for capture of the long distance (by alternating between the current, surface area, and spacing for each mode).

We claim:

1. A neuromodulation system comprising:
   a plurality of neuromodulation electrodes on a common electrode support, the support positionable within a blood vessel to position electrodes within the plurality of electrodes in contact with an interior wall of the blood vessel; and
   a stimulator configured to activate at least a subset of the plurality of electrodes to generate an electric field to capture target nerves disposed external to the blood vessel;
   wherein the system includes
   a mixed nerve capture mode for capturing both parasympathetic and sympathetic nerves, wherein in the mixed nerve capture mode a first combination of the plurality of electrodes is activated to create an anode and a cathode, the anode and cathode in the mixed nerve capture mode having a first separation distance between them, wherein the cathode in the mixed nerve capture mode is comprised of one or more of the electrodes and has a first combined surface area positioned for contact with the blood vessel wall, and
   an independent nerve capture mode, wherein in the independent nerve capture mode a second combination of the plurality of electrodes is activated to create an anode and a cathode having a second separation distance between them, wherein the cathode in the independent nerve capture mode is comprised of one or more of the electrodes and has a second combined surface area positioned for contact with the blood vessel wall, wherein the first separation distance is greater than the second separation distance, and the first combined surface area is greater than the second combined surface area;
   wherein in the mixed nerve capture mode the system generates an electric field that is wider and deeper than an electric field generated by the system in the independent nerve capture mode, and wherein in at least one of the mixed nerve capture mode and the independent nerve capture mode, the cathode is formed from an activated plurality of the plurality of electrodes on the electrode support; and
   wherein the system is configured to capture, in the mixed nerve capture mode, a region of at least one nerve body formed by an anastomosis of both parasympathetic and sympathetic nerves.

2. The system of claim 1, wherein the first separation distance is in the range of 1.5-15 mm.

3. The system of claim 1, wherein the first separation distance is in the range of 2.5-10 mm.

4. The system of claim 2, wherein the first combined surface area is in the range of 3 $mm^2$-10 $mm^2$.

5. The system of claim 3, wherein the second combined surface area is in the range of 3 $mm^2$-10 $mm^2$.

6. The system of claim 1, wherein the stimulator is configured to activate a first plurality of the electrodes to collectively form the anode or cathode.

7. The system of claim 1, wherein the second combined surface area is in the range of 3 $mm^2$-10 $mm^2$.

* * * * *